(12) United States Patent
Canavesi et al.

(10) Patent No.: US 11,844,329 B2
(45) Date of Patent: Dec. 19, 2023

(54) ANIMAL FEEDING AND TRANSPORT DEVICE

(71) Applicant: On Deck Systems, LLC, Beaver, PA (US)

(72) Inventors: Cruz Canavesi, Beaver, PA (US); Brooks Canavesi, Beaver, PA (US)

(73) Assignee: On Deck Systems, LLC, Beaver, PA (US)

( * ) Notice: Subject to any disclaimer, the term of this patent is extended or adjusted under 35 U.S.C. 154(b) by 0 days.

(21) Appl. No.: 17/670,016

(22) Filed: Feb. 11, 2022

(65) Prior Publication Data

US 2022/0256806 A1 Aug. 18, 2022

Related U.S. Application Data

(60) Provisional application No. 63/149,086, filed on Feb. 12, 2021.

(51) Int. Cl.
*A01K 1/06* (2006.01)
(52) U.S. Cl.
CPC .................................. *A01K 1/06* (2013.01)
(58) Field of Classification Search
CPC ................. A01K 1/06; A01K 67/033
See application file for complete search history.

(56) References Cited

U.S. PATENT DOCUMENTS

| | | | | |
|---|---|---|---|---|
| 6,397,782 B1* | 6/2002 | Cope | ................... | A01K 67/033 |
| | | | | 119/475 |
| 9,510,572 B2* | 12/2016 | Aldana | ................ | A01K 67/033 |
| 9,642,344 B2* | 5/2017 | Unger | .................. | A01K 67/033 |
| 10,159,229 B2* | 12/2018 | Marchant | .................. | F21V 7/22 |
| 10,278,368 B1* | 5/2019 | Peeters | .................. | A01K 1/031 |
| 10,292,375 B1* | 5/2019 | Massaro | ................ | B01D 35/02 |
| 2014/0020630 A1* | 1/2014 | Courtright | ............. | A01K 29/00 |
| | | | | 119/6.6 |
| 2015/0122182 A1* | 5/2015 | Aldana | ................ | A01K 67/033 |
| | | | | 119/6.6 |
| 2017/0042131 A1* | 2/2017 | Unger | .................. | A01K 67/033 |
| 2018/0014513 A1* | 1/2018 | Mascari | ................ | A01M 1/023 |
| 2020/0375162 A1* | 12/2020 | Metlitz | ................. | A01K 29/00 |
| 2022/0079126 A1* | 3/2022 | Massaro | ................ | B65B 43/54 |
| 2022/0142137 A1* | 5/2022 | Chase | .................... | A01K 61/85 |

* cited by examiner

*Primary Examiner* — Monica L Perry
*Assistant Examiner* — Aaron M Rodziwicz
(74) *Attorney, Agent, or Firm* — Ulmer & Berne LLP

(57) ABSTRACT

An animal storage and transportation device with an upper enclosure having a floor, a set of supports which elevate the upper enclosure above a horizontal surface, and a primary hole placed within the floor. One or more small animals within the upper enclosure are gravity fed into a transport container via a connection assembly positioned within the primary hole and attached to the floor and an aperture closing mechanism positioned underneath the primary hole which is adapted to open an aperture through which the small animals are transferred.

19 Claims, 6 Drawing Sheets

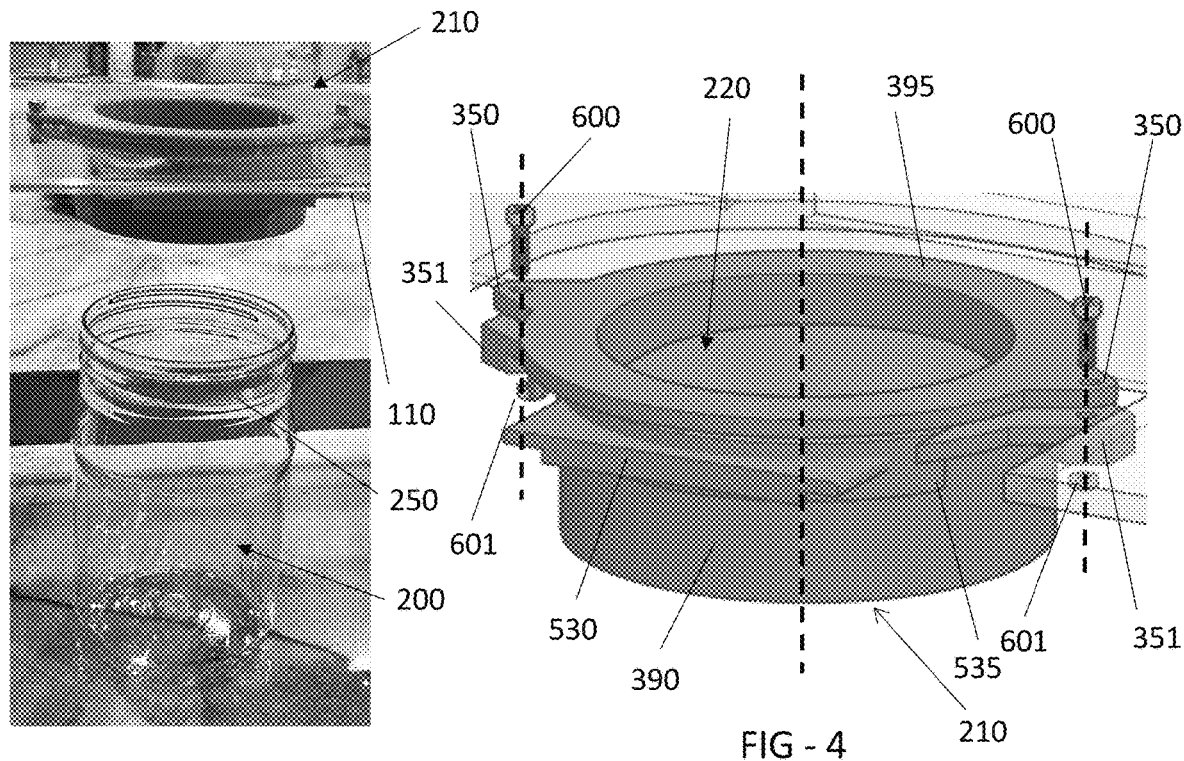
FIG - 3
FIG - 4
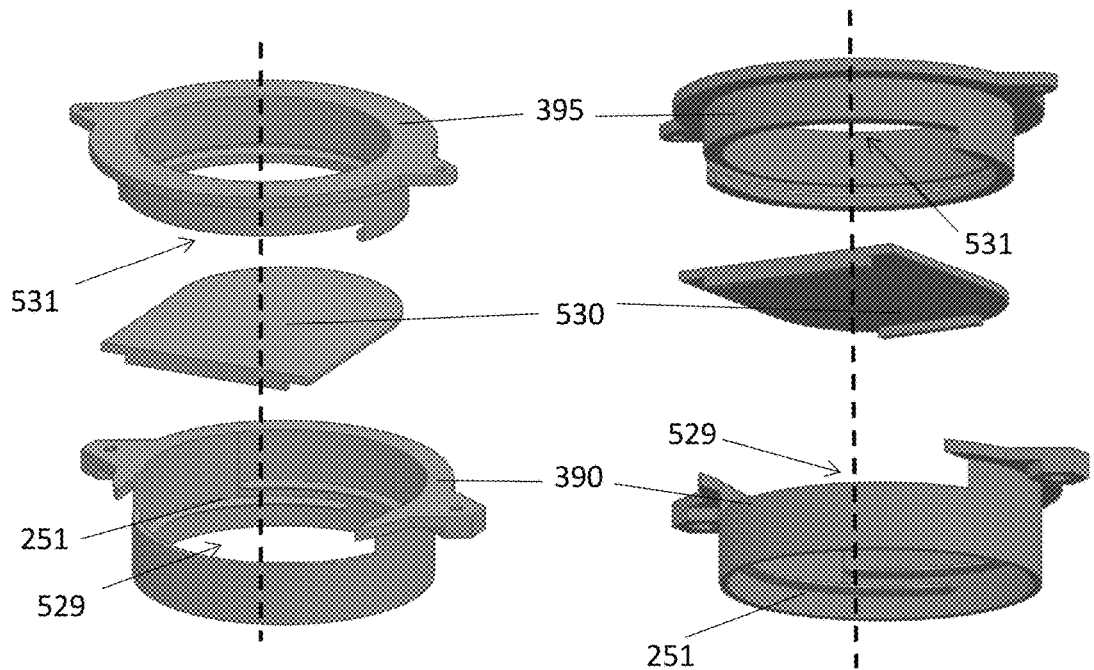
FIG – 5A
FIG – 5B

ANIMAL FEEDING AND TRANSPORT DEVICE

CROSS-REFERENCE TO RELATED APPLICATIONS

This application claims priority to U.S. Provisional Application No. 63/149,086 filed on Feb. 12, 2021 which is herein incorporated by reference in its entirety.

TECHNICAL FIELD

Embodiments generally relate to a device for removing a small animal from a container and transporting it to another location.

BACKGROUND OF THE ART

All types of animals held in some form of captivity/semi-captivity need to be removed from a first enclosure and transported to a second enclosure for a variety of reasons. Additionally, animals held in captivity must be fed and should preferably be fed something as close to their natural diet as possible. However, this is not always as easy as it might seem, especially when feeding a first live animal to a second live animal, there are many problems that can occur. One of the primary issues is handling small animals, which are typically used as food for larger animals. Some of the most common types of small animals used as feed for larger animals are those of the Phylum Arthropada, specifically members of the Class Insecta (commonly referred to as insects), although other members of the Phylum Arthropada can be used as feed, perhaps just not as commonly found as insects.

When storing large numbers of small animals within an enclosure, one of the primary issues is the ability to remove one or a select few of these small animals from the enclosure, while leaving the remainder of the small animals safely within the enclosure. Even once the single or select few animals has been removed, the safe and secure transportation of this small animal to the larger animal as feed can present problems as well. The relatively small size of many of the smaller 'feed' animals can make handling and securing these animals during transport a particularly difficult task.

SUMMARY OF THE EXEMPLARY EMBODIMENTS

Exemplary embodiments provide an upper enclosure which is elevated above a surface and has a floor with an opening. A transport container preferably attaches near the opening in the floor, with an aperture closing mechanism positioned between the transport container and the interior of the upper enclosure. This mechanism can open/close an aperture, which allows one or more animals in the upper enclosure to fall into the transport container. A collar on the transport container preferably engages with a connection assembly that is attached to the floor, and this engagement is a removable engagement so that the transport container can be attached and removed from the connection assembly (i.e. upper enclosure). Prior to removing the transport container, the aperture may be closed, to ensure that no animals can escape the upper enclosure while the transport container is detached and transporting one or more small animals. The transport container could be immediately re-attached once the small animals are transported to a second location, or could be set aside until it is necessary to remove another small animal(s) from the upper enclosure.

The foregoing and other features and advantages of the present invention will be apparent from the following more detailed description of the particular embodiments, as illustrated in the accompanying drawings.

BRIEF DESCRIPTION OF THE DRAWINGS

A better understanding of an exemplary embodiment will be obtained from a reading of the following detailed description and the accompanying drawings wherein identical reference characters refer to identical parts and in which:

FIG. 3 is a front perspective view of Detail A after the transport container has been detached from the connection assembly.

FIG. 4 is a front partially exploded view showing the connection assembly and aperture closing mechanism, where mechanical fasteners are shown exploded along their central axis for clarity.

FIG. 5A is a top exploded view of the connection assembly and aperture closing mechanism of FIG. 4, shown exploded along their shared central axis.

FIG. 5B is a bottom exploded view of the connection assembly and aperture closing mechanism of FIG. 4, shown exploded along their shared central axis.

DETAILED DESCRIPTION

Figure 1:
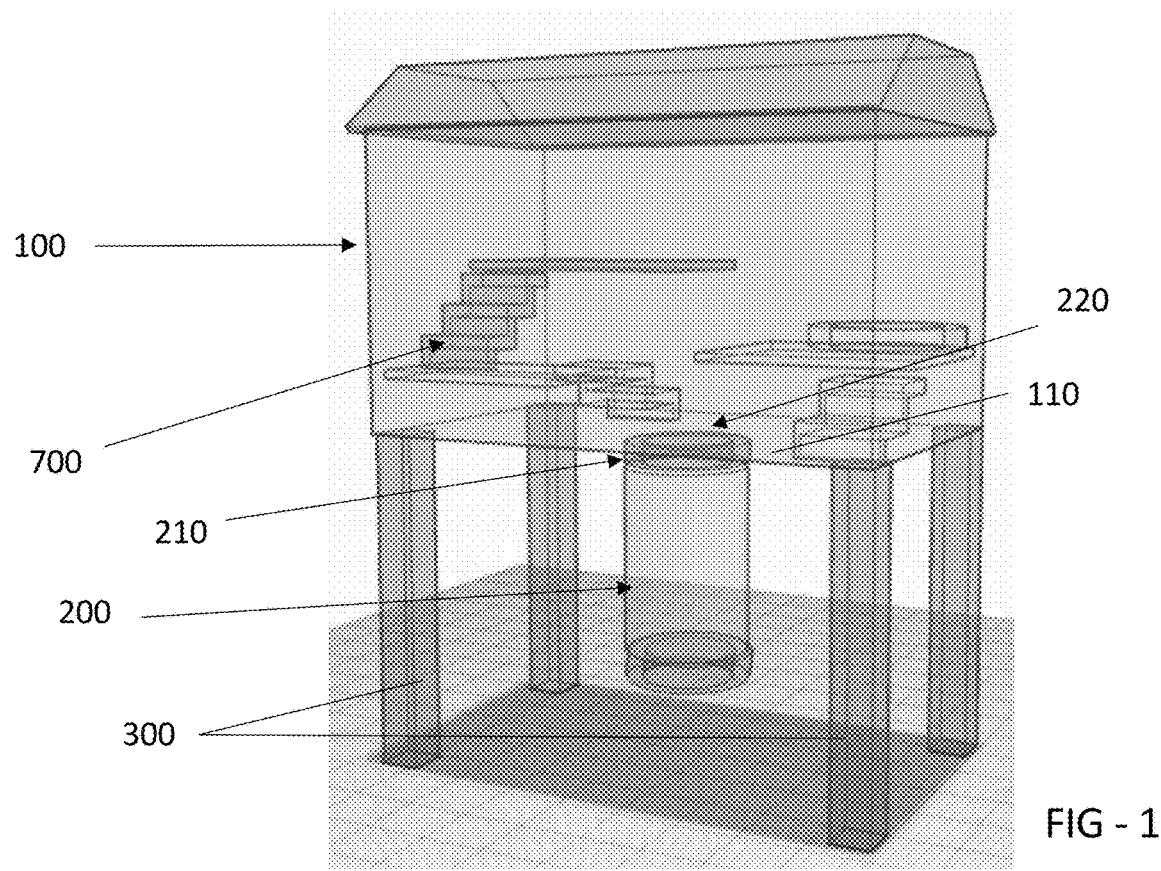
FIG. 1 is a perspective view of an exemplary embodiment of a transport container attached to the floor of an upper enclosure.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a perspective illustration of an exemplary transport container 200 attached to the underside of an upper enclosure 100 which preferably contains a plurality of interior structures 700 for the small animals to climb, move, and be positioned to be removed through the aperture (shown below). Of course any number or type of interior structures 700 may be used, as the design shown is simply provided as an example.

In this particular embodiment, four support legs 300 are used to hold the upper enclosure 100 at an elevated position above the horizontal surface. The transport container 200 preferably contains a top portion which engages with a connection assembly 210 in order to removably connect the transport container 200 to the upper enclosure 100.

Figure 2:
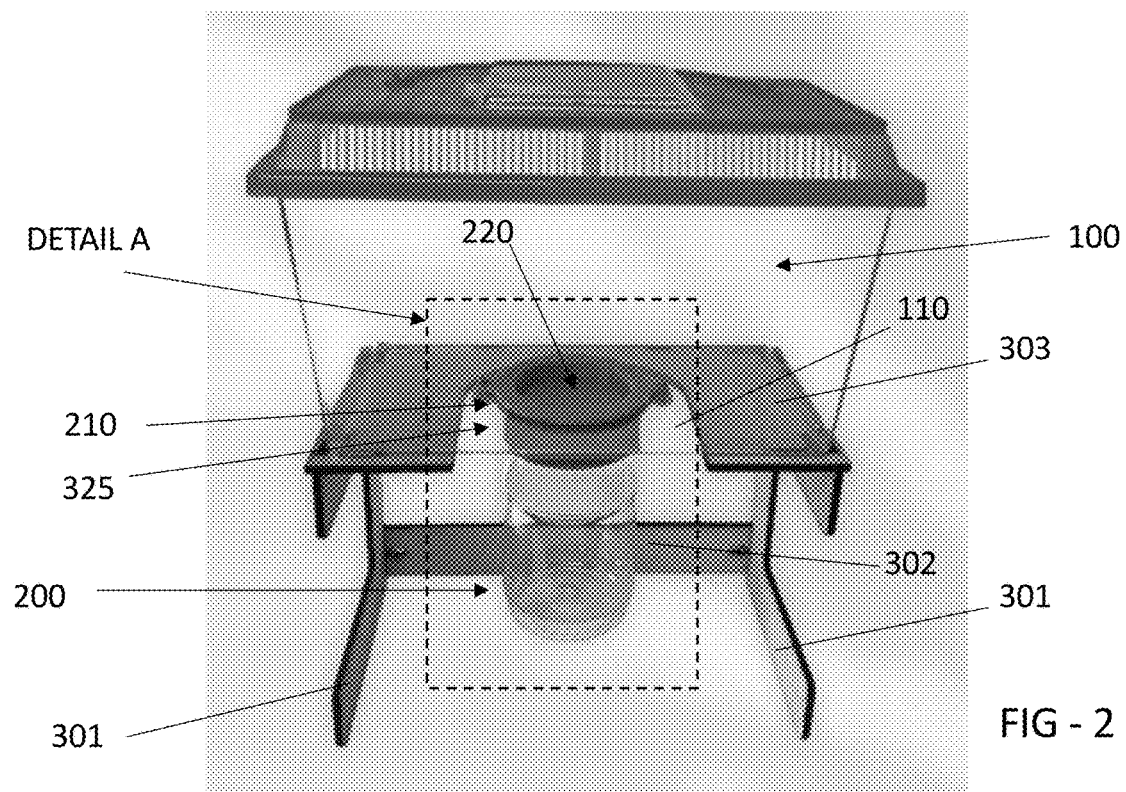
FIG. 2 is a front perspective view of another embodiment of a transport container attached to the floor of an upper enclosure, and providing the location for Detail A.

FIG. 2 is a front perspective view of another embodiment of a transport container 200 attached to the floor 110 of an upper enclosure 100, and providing the location for Detail A. In this embodiment, a pair of U-shaped side supports 301 are connected to an elongate support element 302 to elevate and support a horizontal platform 303 above a horizontal surface. The floor 110 of the upper enclosure 100 preferably rests atop the platform 303. The connection assembly 210 is preferably sized to fit within a primary hole 325 within the floor 110. An aperture closing mechanism 220 is capable of opening/closing an aperture to allow small animals to be gravity fed from the upper enclosure 100 into the transport container 200.

FIG. 3 is a front perspective view of Detail A after the transport container 200 has been detached from the connection assembly 210. In this embodiment, the transport container 200 preferably contains a set of male threads 250 at the top portion of the container. These male threads 250 are positioned and sized to be accepted into corresponding female threads 251 (shown below) found on the underside of the connection assembly 210. In this way, the transport container 200 can be connected/disconnected to the connection assembly 210 by rotating the transport container 200 about its central axis so that male threads 250 engage with female threads 251 found on the underside of the connection assembly 210.

FIG. 4 is a front partially exploded view showing the connection assembly 210 and aperture closing mechanism 220, where mechanical fasteners 600/601 are shown exploded along their central axis for clarity. In this embodiment, the connection assembly 210 comprises an upper ring 395 which aligns with the central axis of a lower ring 390. The upper ring 395 preferably contains a pair of opposing tabs 350 which extend radially from opposing sides of the upper ring 395 to provide an aperture for accepting male mechanical fastener 600. Similarly, the lower ring 390 preferably contains a pair of opposing tabs 351 which extend radially from opposing sides of the lower ring 390 to provide an aperture for accepting female mechanical fastener 600.

When aligning the upper ring 395 with the lower ring 390, the central axis of each ring should be aligned as well as the axis of the apertures within each tab 350 and 351. Once properly aligned, the male fasteners 600 can be attached to the female fasteners 601 in order to squeeze (sandwich) the floor 110 in between the upper ring 395 and lower ring 390. In this embodiment, a thin plate 530 can slide horizontally in between the upper ring 395 and lower ring 390. This thin plate 530 is translated in a direction substantially perpendicular to the central axis of the transport container 200 in order to open/close the aperture 230 to allow a small animal to be gravity fed through the floor 110 of the upper enclosure 100 and into the transport container 200.

FIG. 5A is a top exploded view of the connection assembly 210 and aperture closing mechanism 220 of FIG. 4, shown exploded along their shared central axis.

FIG. 5B is a bottom exploded view of the connection assembly 210 and aperture closing mechanism 220 of FIG. 4, shown exploded along their shared central axis. A slot 535 for accepting the thin plate 530 is generally defined with an upper notch 531 formed into the underside of the upper ring 395, and a corresponding lower notch 529 formed into the topside of the lower ring 390. When combined together, the upper notch 531 and lower notch 529 define a slot 535 that is slightly larger than the thin plate 530, allowing the thin plate 530 to move horizontally back and forth through the slot 535.

Figure 6:
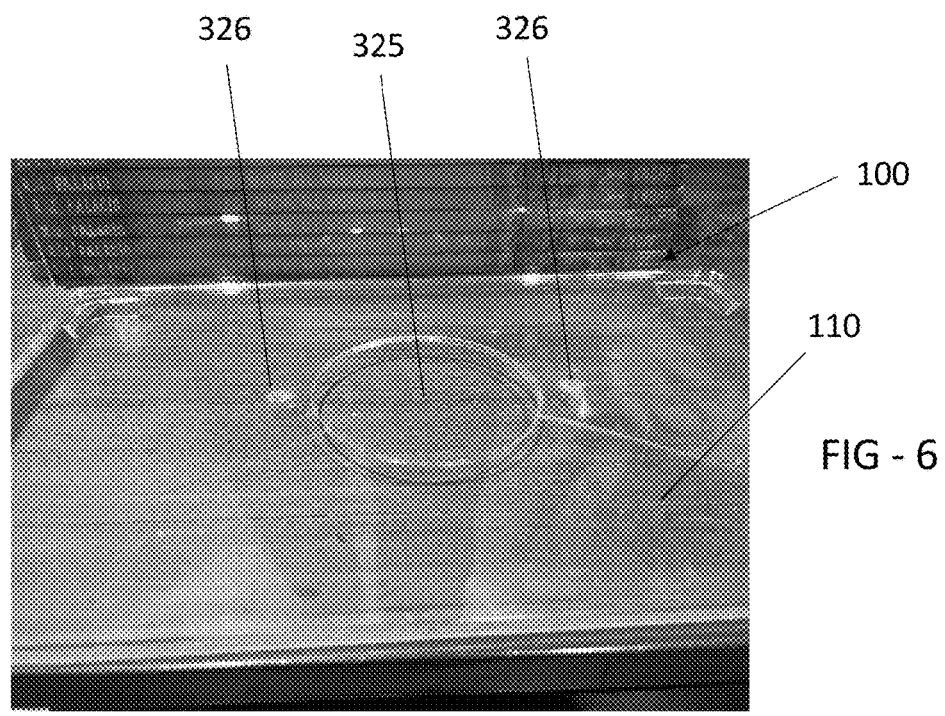
FIG. 6 is a top perspective view of one embodiment for the upper enclosure corresponding to the connection assembly and aperture closing mechanism of FIG. 4.

FIG. 6 is a top perspective view of one embodiment for the upper enclosure 100 corresponding to the connection assembly 210 and aperture closing mechanism 220 of FIG. 4. A primary hole 325 is placed in the floor 110, and is preferably sized to be slightly larger than the outer diameter of the upper ring 395. While not required for other embodiments, this particular embodiment also uses a pair of pass through holes 326 which allow the male fasteners 600 to pass through the floor 110 and connect with the female fasteners 601. In this way, the upper ring 395 fills the space of the primary hole 325 and does not allow any space (other than the aperture 230) for small animals to escape the upper enclosure 100.

Figure 7:
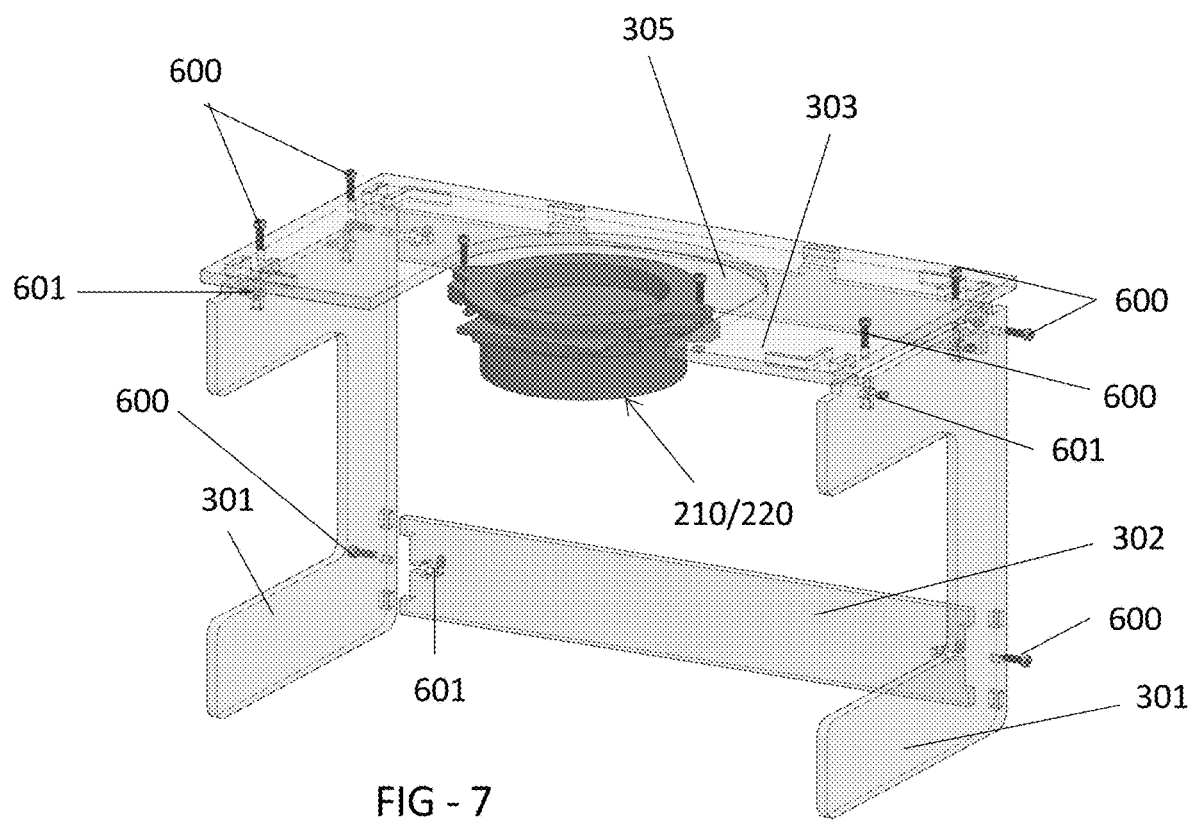
FIG. 7 is a front perspective view of the embodiment shown in FIG. 2, where the upper enclosure and transport container have been removed.

FIG. 7 is a front perspective view of the embodiment shown in FIG. 2, where the upper enclosure 100 and transport container 200 have been removed. As noted above, for this embodiment a pair of U-shaped sides 301 are connected to an elongate element 302 to support a horizontal platform 303 which is elevated above a horizontal surface. The U-shaped sides 301 are preferably connected to the elongate element 302 and horizontal platform 303 using male mechanical fasteners 600 which engage with female mechanical fasteners 601. An optional additional elongate element 305 may be used to connect between the upper portion of the U-shaped sides 301.

Figure 8A:
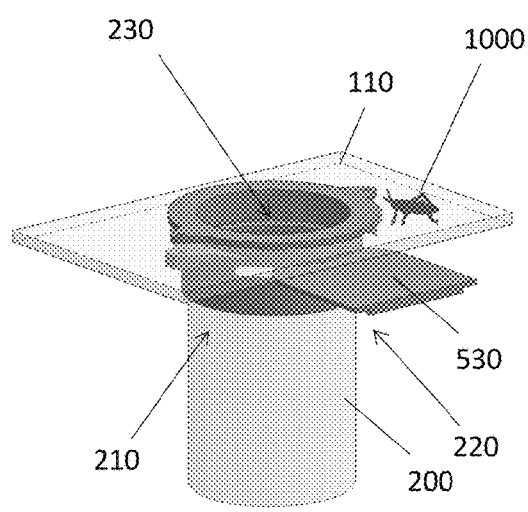
FIG. 8A is a top perspective view of Detail A showing the aperture closing mechanism in a state of open, ready to accept a small animal.

FIG. 8A is a top perspective view of Detail A showing the aperture closing mechanism 220 in a state of open, ready to accept a small animal 1000. Since the thin plate 530 remains mostly outside of the slot in the rings 395/390, the aperture 230 remains mostly open.

Figure 8B:
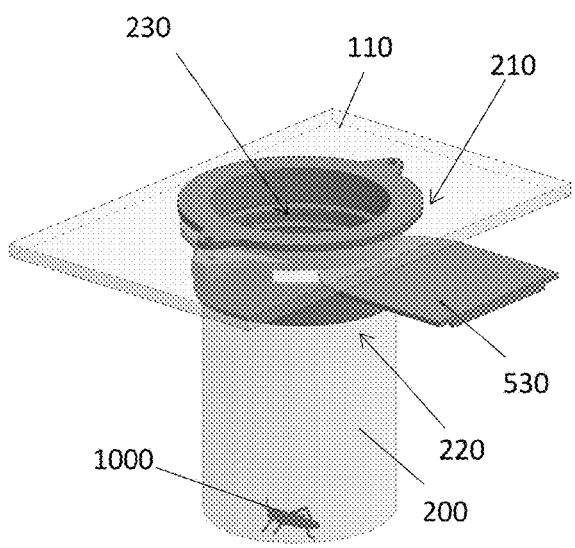
FIG. 8B is a top perspective view of Detail A showing the aperture closing mechanism in a state of open, with a small animal having been received into the transport container.

FIG. 8B is a top perspective view of Detail A showing the aperture closing mechanism 220 in a state of open, with a small animal 1000 having been received into the transport container 200. Here, the animal 1000 has been gravity fed down into the transport container 200.

Figure 8C:
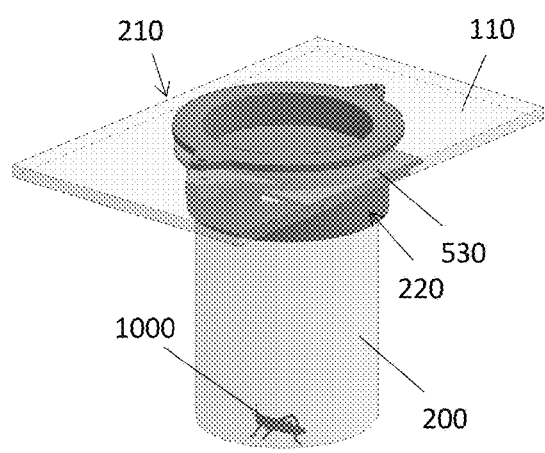
FIG. 8C is a top perspective view of Detail A showing the aperture closing mechanism in a state of closed.

FIG. 8C is a top perspective view of Detail A showing the aperture closing mechanism 220 in a state of closed. Having received the desired number of small animals 1000 into the container 200, the thin plate 530 can now slide deeper into the slot between the rings 395/390, which closes the aperture 230 to prevent further animals 1000 from being gravity fed.

Figure 8D:
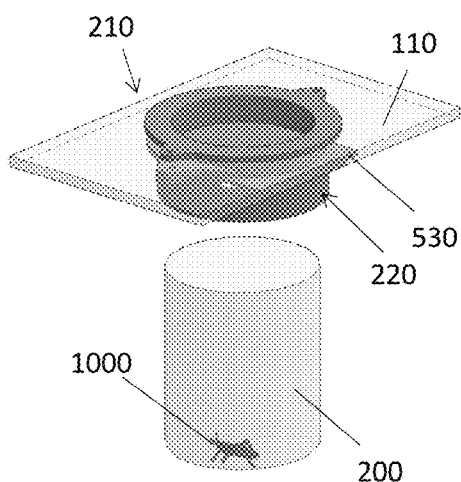
FIG. 8D is a top perspective view of Detail A showing the aperture closing mechanism in a state of closed, where the transport container having a small animal is disconnected from the connection assembly.

FIG. 8D is a top perspective view of Detail A showing the aperture closing mechanism 220 in a state of closed, where the transport container 200 (now having a small animal 1000 contained inside) is disconnected from the connection assembly 220. Now the small animal 1000 can easily be transported to another location. In most cases, the small animal 1000 cannot escape the transport container 200, but if there is any doubt the user can place their hand over the top opening of the transport container 200 while the small animal 1000 remains in the container 200 during transport.

Figure 9:
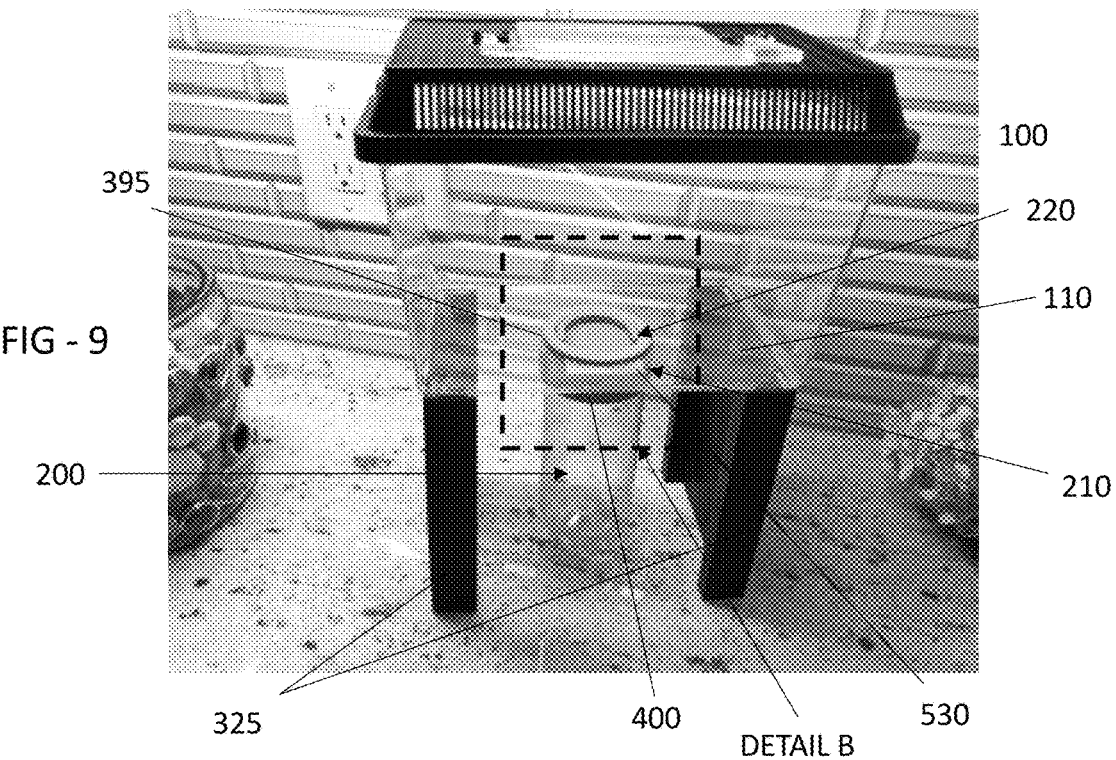
FIG. 9 is a top perspective view of another embodiment of a transport container attached to the floor of an upper enclosure, and indicating the location of Detail B.

FIG. 9 is a top perspective view of another embodiment of a transport container 400 attached to the floor 110 of an upper enclosure 100, and indicating the location of Detail B. Similar to other embodiments, the connection assembly 210 preferably engages with the floor 110 of the upper enclosure 100 and may have components positioned both above and below the floor 110 in order to squeeze or otherwise engage with the floor 110. In other embodiments the connection assembly 210 may have components only above or only below the floor 110, and may use mechanical fasteners to attach to the floor 110.

Generally speaking, the connection assembly 210 allows the transport container 200 to attach with and preferably seal with the floor 110, while it does not have to be a water tight seal it should be a tight enough seal so that animals contained within the upper enclosure 100 could not escape (i.e. no longer confined by either the upper enclosure 100 or the transport container 200). An aperture 230 is opened and closed through an aperture closing mechanism 220, which can be either above or below the floor 110.

Figure 10:
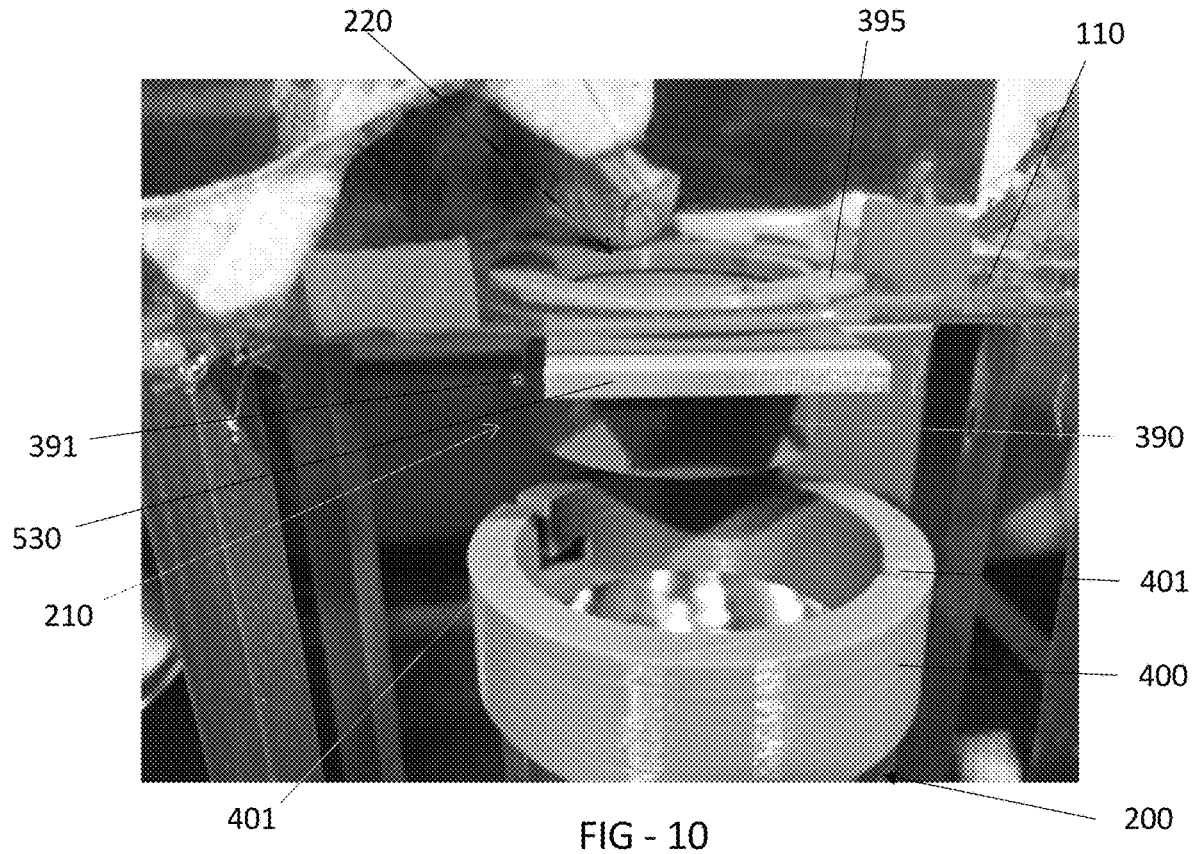
FIG. 10 is a detailed perspective view of Detail B where the collar of the transport container has been disconnected from the connection assembly.

FIG. 10 is a detailed perspective view of Detail B where the collar 400 of the transport container 200 has been disconnected from the connection assembly 210. In this embodiment, the thin plate 530 is translated in a direction substantially perpendicular to the central axis of the transport container 200 in order to open/close the aperture 230. The thin plate 530 contains a portion which is exposed to the inside of the upper enclosure 100 and another portion which is outside of the upper enclosure 100 so that it can be grasped by a user and translated away from the upper enclosure 100 in order to open the aperture 230 and accept a small animal.

Figure 11:
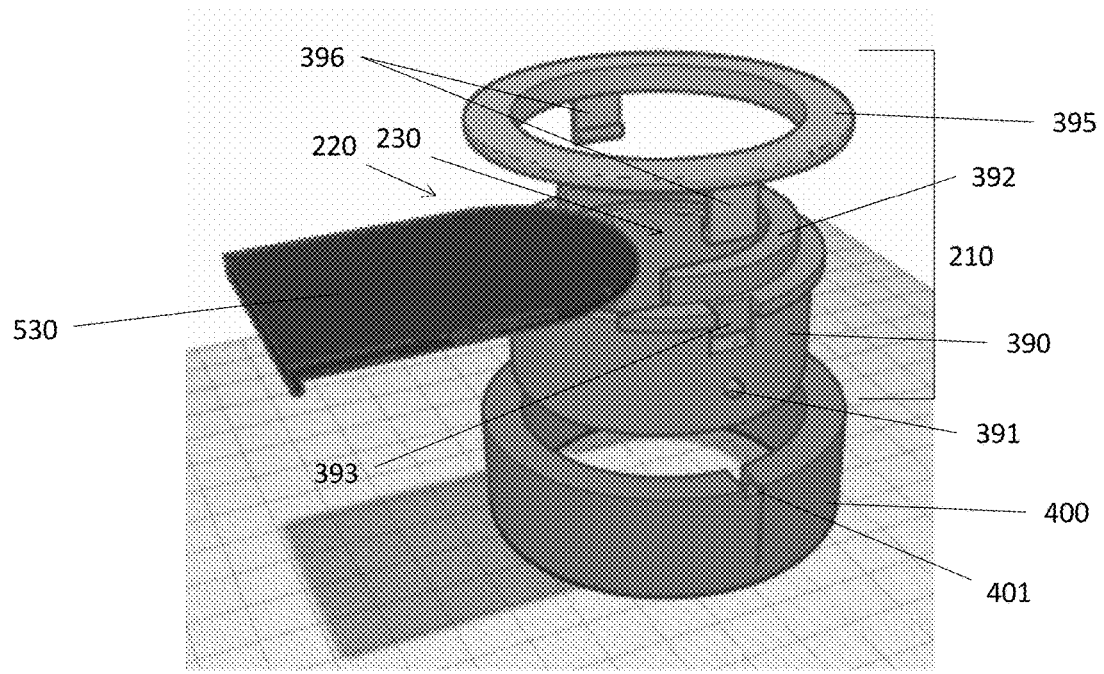
FIG. 11 is an exploded view of the exemplary embodiments of a connection assembly and aperture closing mechanism shown in FIGS. 9 and 10.

FIG. 11 is an exploded view of the exemplary embodiments of a connection assembly 210 and aperture closing mechanism 220 shown in FIGS. 9 and 10. Here we can see the details for this embodiment of the connection assembly 210, which is generally comprised of an upper ring 395 which connects to a lower ring 390. In this embodiment, the top ring 395 contains a pair of tabs 396 which extend downwardly from the ring 395 which is substantially flat. Accordingly, the lower ring 390 contains a pair of receiving apertures 393 which accept the tabs 396, in this way the floor 110 is sandwiched between the upper ring 395 and lower ring 390, securing the connection assembly 210 to the floor 110. Of course, other designs for the mechanical connection of the upper ring 395 to the lower ring 390 can be used, any type of extended portion on one of the rings which engages with a receiving aperture on the opposing ring with some small interference or 'snap fit' would be acceptable to hold the two pieces to the floor 110. Mechanical fasteners could also be used to accomplish this. In this embodiment, a rounded receiving slot 392 also preferably extends upwardly from the top surface of the lower ring 390 and accepts a peripheral edge portion of the thin plate 530. In this embodiment, the edge portion of the thin plate 530 that engages with the slot 395 has a curved radius (which generally matches a radius of the receiving slot 392) while the portion of the thin plate 530 that is grasped by the user has more of a rectangular shape. Thus, preferably a rectangular edge is positioned at a first end of the thin plate 530 and a rounded edge is positioned at a second end of the thin plate 530.

Figure 12:
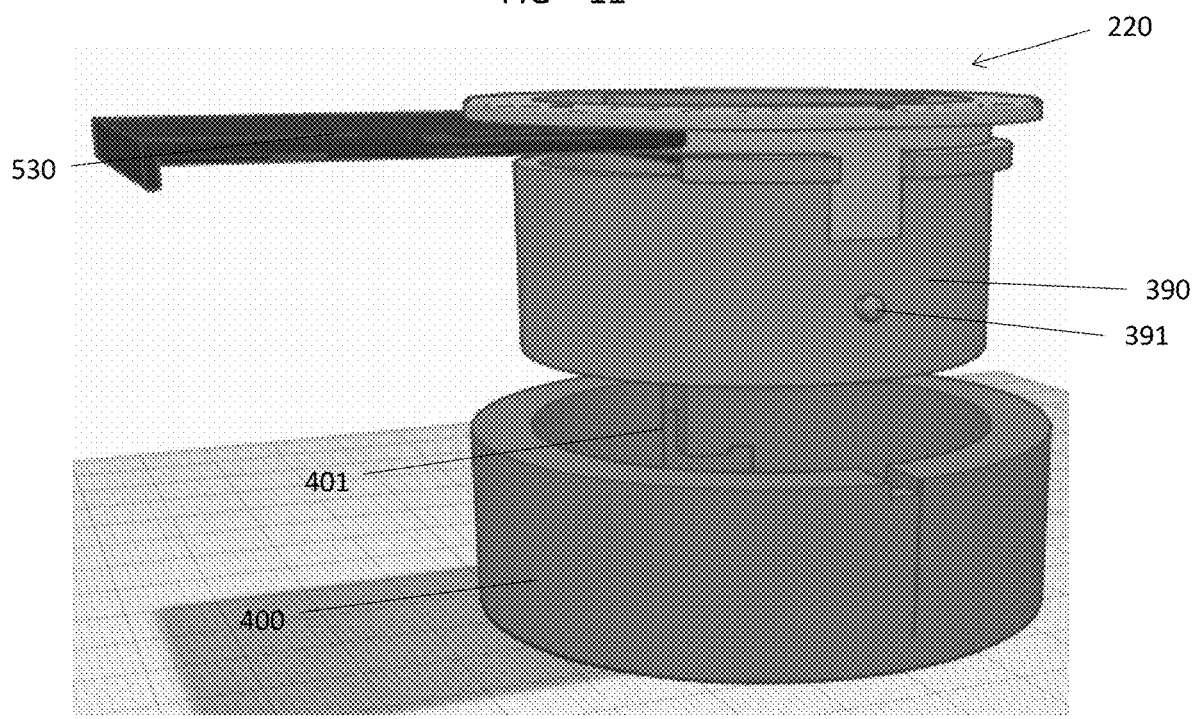
FIG. 12 is a partially exploded view of the exemplary embodiments of a connection assembly and aperture closing mechanism shown in FIGS. 9 and 10.

FIG. 12 is a partially exploded view of the exemplary embodiments of a connection assembly 210 and aperture closing mechanism 220 shown in FIGS. 9 and 10. In this embodiment, the lower ring 390 contains a stud 391 which extends from the exterior sidewall of the lower ring 390. In order to removably secure the transport container 200 to the upper enclosure 100, the stud 391 preferably engages mechanically with a slot 401 in the collar 400 which is attached to a top portion of the transport container 200. As shown here, it is preferable that the slot 401 would have an "L" shape so that the stud 391 can be received and then engaged with the horizontal portion of the "L" when the transport container 200 is rotated about its central axis relative to the upper enclosure 100. It should be noted that this is only one mechanical solution, while many others could be used and would be within this invention, specifically other shapes of slots as well as a screw or thread-type mechanism would be acceptable alternatives.

The aperture closing mechanism 220 shown in FIG. 12, showing the aperture 230 open so that a small animal can drop from the upper enclosure 100 into the transport container 200 (in this way, it could be said that the transport container 200 is gravity fed with any small animal that is positioned immediately above the aperture 230). Although the collar 400 of the transport container 200 is shown as disconnected from the lower ring 390 in this image, it would preferably be connected to the lower ring 390 while a small animal is being removed from the upper enclosure 100, to ensure that the animal cannot escape through any separation between the lower ring 390 and the collar 400.

A user can slide the thin plate 530 horizontally after a small animal has dropped from the upper enclosure 100 into the transport container 200. The collar 400 of the transport container 200 is shown as disconnected from the lower ring 390, so that the transport container 200 can be removed and the small animal(s) inside can be transported to another location. It has been discovered that if the transport container 200 is sufficiently deep enough with smooth sidewalls, most small animals placed in the transport container 200 are not able to escape as long as the container 200 is help upright with the collar 400 facing upwards. It has been discovered that most animals are not able to climb the vertical walls of the transport container 200, provided that the interior surfaces are sufficiently smooth, and therefore an aperture or closing mechanism is not generally necessary for the transport container 200 itself, to ensure that small animals do not escape during transport.

In FIG. 12, the slot 401 on the interior surface of the collar 400 is shown. In the embodiment shown, the slot 401 does not cut all the way through the collar 400, but this is not required. Generally, all that is required is that the slot 401 is cut into the collar 400 at a depth that is slightly greater than the distance that the stud 391 extends outwardly from the outer surface of the lower ring 390. In other embodiments, the slot 401 could be cut deeper than what is shown here, and in some embodiments it could cut all the way through the collar 400.

While some embodiments for the aperture closing mechanism 220 have been specifically shown and described herein, this element can take on many forms and would still be within the scope of the invention. Specifically, other embodiments would use rounded flower petal shapes, a plurality of spiral wedges, a plurality of triangular wedges, or any combination of cams and surfaces that move in order to open/close the aperture 230 for accepting a small animal. Other embodiments are specifically shown in FIGS. 6-11B of Provisional Application No. 63/149,086 filed on Feb. 12, 2021 which are herein incorporated by reference.

The various components herein could be constructed out of any combination of plastics, metals, or composite/hybrid materials, depending on the application.

As used herein, the term 'small animals' refers to all members of the Kingdom Animalia that are small enough to be contained within an enclosure and needs to be transported occasionally into another enclosure. As used herein the term 'small animals' would also specifically include all members of Phylum Arthropada, all members of Class Insecta, worms, crickets, spiders, scorpions, butterflies, dragon flies, wasps, and all similar animals.

Having shown and described a preferred embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

We claim:

1. An animal storage and transportation device comprising:
   an upper enclosure having a floor;
   a set of supports which elevate the upper enclosure above a horizontal surface;
   a primary hole placed within the floor;
   a connection assembly positioned within the primary hole and having
     an upper ring; and
     a lower ring,
     wherein the upper ring and the lower ring connect together to sandwich the floor in between the upper ring and lower ring;
   a transport container removably connected to the connection assembly; and
   an aperture closing mechanism positioned underneath the primary hole which is adapted to open an aperture which allows one or more small animals within the upper enclosure to be gravity fed into the transport container.

2. The device of claim 1 further comprising:
   female threads positioned on an underside of the connection assembly; and
   male threads positioned near a top portion of the transport container; where the male threads are sized to removably engage with the female threads.

3. The device of claim 1 wherein:
   the aperture closing mechanism comprises a thin plate that slides horizontally.

4. The device of claim 3 further comprising:
   a slot in the connection assembly sized to allow the thin plate to slide through said slot.

5. The device of claim 4 further comprising:
   a collar attached to an upper portion of the transport container and adapted to removably connect with the connection assembly.

6. The device of claim 4 further comprising:
   a stud extending outwardly from the connection assembly; and
   a notch within the collar which is sized to accept the stud.

7. The device of claim 3 further comprising:
   a rounded receiving slot in the connection assembly sized to receive a rounded edge portion of the thin plate.

8. The device of claim 3 further comprising:
   a rectangular edge positioned at a first end of the thin plate; and
   a rounded edge positioned at a second end of the thin plate.

9. The device of claim 1 further comprising:
   a pair of opposing tabs extending radially from the upper ring; and
   a pair of opposing tabs extending radially from the lower ring.

10. The device of claim 1 further comprising:
    a pair of tabs on the upper ring that extend downwardly; and
    a pair of receiving apertures on the lower ring, each one accepting one of the tabs extending from the upper ring.

11. The device of claim 1 wherein:
    the aperture closing mechanism is a cam that controls a plurality of spiral wedges.

12. An animal storage and transportation device for use with an upper enclosure having a floor and a primary hole placed within the floor, the device comprising:
    a set of supports which elevate the upper enclosure above a horizontal surface;
    a connection assembly adapted to be placed within the primary hole and attached to the floor;
    a transport container removably connected to the connection assembly; and
    an aperture closing mechanism positioned over the primary hole which is adapted to open an aperture which allows one or more small animals within the upper enclosure to be gravity fed into the transport container.

13. The device of claim 12 wherein:
    the connection assembly comprises an upper ring and lower ring which connect together to sandwich the floor in between the upper ring and lower ring.

14. The device of claim 12 wherein:
    the aperture closing mechanism comprises a thin plate that slides horizontally through a slot in the connection assembly.

15. The device of claim 12 further comprising:
female threads positioned on an underside of the connection assembly; and
male threads positioned near a top portion of the transport container; where the male threads are sized to removably engage with the female threads.

16. An animal storage and transportation device comprising:
an upper enclosure having a floor;
a set of supports which elevate the upper enclosure above a horizontal surface;
a primary hole placed within the floor;
a connection assembly positioned within the primary hole and having
an upper ring with a portion above the floor;
a lower ring with a portion beneath the floor;
where the upper ring is attached to the lower ring thereby squeezing the floor in between the upper ring and lower ring;
a slot defined by a space between the upper ring and lower ring;
a transport container removably connected to the connection assembly; and
a thin plate positioned underneath the primary hole and sized to slide horizontally within the slot to open and close an aperture which allows one or more small animals within the upper enclosure to be gravity fed into the transport container.

17. The device of claim 16 further comprising:
a pair of opposing tabs extending radially from the upper ring; and
a pair of opposing tabs extending radially from the lower ring,
where the tabs on the upper ring are aligned with the tabs on the lower ring.

18. The device of claim 16 further comprising:
female threads positioned on an underside of the lower ring; and
male threads positioned near a top portion of the transport container; where the male threads are sized to removably engage with the female threads.

19. The device of claim 16 wherein:
the set of supports comprises a pair of U-shaped sides which connect to an elongate element to support a horizontal platform, where the floor rests atop the horizontal platform.

* * * * *